United States Patent

Nakazawa et al.

[11] Patent Number: 5,683,231
[45] Date of Patent: Nov. 4, 1997

[54] BLOOD PUMP HAVING MAGNETIC ATTRACTION FORCE ADJUSTER

[75] Inventors: Tadashi Nakazawa; Yoshiyuki Takami; Kenzo Makinouchi; Yukihiko Nosé, all of Houston, Tex.

[73] Assignee: Kyocera Corporation, Kyoto, Japan

[21] Appl. No.: 675,014

[22] Filed: Jul. 3, 1996

Related U.S. Application Data

[62] Division of Ser. No. 512,307, Aug. 8, 1995, Pat. No. 5,575,630.

[51] Int. Cl.$^6$ ................................................ F04B 17/03
[52] U.S. Cl. .................... 417/420; 415/900; 417/423.12
[58] Field of Search .............................. 417/420, 423.1, 417/423.7, 423.12; 604/151; 415/900; 384/907.1, 913, 908

[56] References Cited

U.S. PATENT DOCUMENTS

| | | | |
|---|---|---|---|
| 3,932,069 | 1/1976 | Giardini et al. | 417/420 |
| 4,507,048 | 3/1985 | Belenger | 415/90 |
| 4,643,641 | 2/1987 | Clausen et al. | 415/900 |
| 4,806,080 | 2/1989 | Mizobuchi et al. | 417/423.15 |
| 4,874,300 | 10/1989 | Laing et al. | 417/420 |
| 4,898,518 | 2/1990 | Hubbard et al. | 417/360 |
| 5,049,134 | 9/1991 | Golding et al. | 415/900 |
| 5,055,005 | 10/1991 | Kletschka | 415/900 |
| 5,079,467 | 1/1992 | Dorman | 417/360 |
| 5,253,986 | 10/1993 | Bond et al. | 417/420 |
| 5,360,317 | 11/1994 | Clausen et al. | 415/900 |
| 5,399,074 | 3/1995 | Nose et al. | 417/423.14 |
| 5,458,459 | 10/1995 | Hubbard et al. | 415/900 |

*Primary Examiner*—Timothy Thorpe
*Assistant Examiner*—Peter G. Korytnyk
*Attorney, Agent, or Firm*—Loeb & Loeb LLP

[57] ABSTRACT

A blood pump used for heart-lung machines comprising an impeller, a casing having a suction inlet and a delivery outlet and rotatably encasing the impeller, a magnetic driver disposed outside the casing, and a magnetic attraction force adjuster. The impeller has a rotationally symmetric shape, such as a conical shape, is equipped with vanes having a pumping function on the side surface thereof and is also equipped with magnets, such as permanent magnets. The magnetic driver for rotating the impeller in cooperation with the magnets comprises a magnet assembly magnetically connected to the magnets and a rotation driver for rotating the magnet assembly. The magnetic attraction force adjuster adjusts the magnetic attraction force generated between the magnets and the magnet assembly by adjusting the gap between the magnets and the magnet assembly or by adjusting the exciting current of electromagnets when electromagnets are used for the magnet assembly. One of the pivot and pivot bearing for supporting the rotation shaft of the impeller is made of ceramics and the other is made of synthetic resin.

1 Claim, 11 Drawing Sheets

BLOOD PUMP HAVING MAGNETIC ATTRACTION FORCE ADJUSTER

This is a division of application Ser. No. 08/512,307 filed on Aug. 8, 1995 now U.S. Pat. No. 5,575,630.

BACKGROUND OF THE INVENTION

1. Field of the Invention

The present invention relates to a blood pump used for heart-lung machines or the like.

2. Prior Arts

In recent years, centrifugal blood pumps have begun to be used widely as blood circulation pumps for heart-lung machines.

In the case of the centrifugal blood pump described in U.S. Pat. No. 4,507,048, a nearly conical impeller with side vanes equipped with a magnetic means, such as permanent magnets, on the bottom surface side thereof is supported at pivots located at the upper and lower ends of the rotation shaft thereof by the pivot bearings of the casing which encases the impeller and is provided with a suction inlet and a delivery outlet. A magnetic drive means, such as an electric winding for generating a rotating magnetic field, being disposed outside the casing opposite to the above-mentioned magnetic means with the casing interposed therebetween in order to rotate the impeller in cooperation with the magnetic means.

In this kind of blood pump, the impeller is attracted to the bottom surface of the casing by the magnetic attraction force generated between the magnetic means disposed on the bottom side of the impeller and the magnetic drive means disposed opposite to the magnetic means with the casing interposed therebetween. When the rotation speed of the impeller is low, the impeller rotates mainly supported by the pivot at the lower end of the rotation shaft thereof and the bearing for the pivot. When the rotation speed of the impeller increases, the blood pressure in the casing becomes low at the upper side of the impeller and becomes high at the lower side thereof, thereby generating lifting force to the impeller. When this lifting force exceeds the magnetic attraction force, the impeller becomes supported mainly by the pivot disposed at the upper end of the rotation shaft and the bearing for the pivot. When the magnetic attraction force is balanced with the lifting force, the impeller is in a weightless condition, and the impeller performs ideal rotation wherein no great force is applied to the pivot bearing.

In the above-mentioned conventional blood pump, however, since the gap between the magnetic means disposed on the impeller and the magnetic drive means disposed outside the casing opposite to the magnetic means is set to a fixed value, the magnetic attraction force generated therebetween is constant. However, the above-mentioned impeller lifting force is changed by pump operation conditions, such as impeller rotation speed and blood flow rate. For this reason, it is difficult to balance the magnetic attraction force with the lifting force. In addition, the rotation of the impeller becomes unstable depending on the operation conditions of the pump, causing a problem of generating vibration on the impeller. In particular, when the rotation shaft of the impeller is supported by the pivot and the bearing for the pivot, the curvature radius R of the bearing support surface is usually made far larger than the curvature radius r of the pivot tip as shown in FIG. 2. Since the pivot is not supported in the radial direction thereof, the pivot is apt to generate vibratory rotation, thereby significantly causing the above-mentioned problem.

When the impeller vibrates, blood cells in blood are destroyed and more hemolysis is caused. Furthermore, the pivot and the bearing for the pivot are worn greatly, thereby causing a problem of making continuous operation for an extended period of time difficult.

Moreover, if axial dislocation or inclination is generated between the rotation center axis of the magnetic means of the impeller and the center axis of the magnetic drive means disposed outside the casing, opposite to the magnetic means, the magnetic attraction force generated during impeller rotation does not become uniform, thereby making impeller rotation unstable and causing problems similar to those described above.

In U.S. Pat. No. 5,399,074, the applicants of the present invention have proposed that the pivot or the bearing for the pivot at the rotation shaft lower end of the impeller of the blood pump should be made of ceramics. The specification of the Unites States Patent has also disclosed that at least the pivot or the bearing of each of the pivot-bearing combinations is desired to be made of ceramics (in line 39 of column 6 and the following descriptions). However, if both the pivot at the rotation shaft end of the impeller and the bearing for supporting the pivot are made of ceramics, these members are worn significantly during impeller rotation. As a result, impeller rotation becomes unstable during operation for an extended period of time, thereby causing problems similar to those described above.

SUMMARY OF THE INVENTION

The present invention is intended to solve the above-mentioned problems encountered in blood pumps. An object of the present invention is to provide a blood pump ensuring stable impeller rotation and capable of operating continuously for an extended period of time.

Another object of the present invention is to provide a blood pump ensuring stable impeller rotation and causing less hemolysis during operation.

Still another object of the present invention is to provide a blood pump generating less wear at the pivot used to rotatably support the impeller and the bearing for the pivot, and capable of operating stably for an extended period of time.

A further object of the present invention is to provide a blood pump wherein the magnetic attraction force generated between the magnetic means provided on the impeller and the magnetic drive means disposed outside the casing opposite to the magnetic means is balanced with the lifting force applied to the impeller during pump operation in order to make stable impeller rotation possible.

To achieve the above-mentioned objects, the blood pump of the present invention comprises an impeller, a casing having a suction inlet and a delivery outlet and rotatably encasing the impeller, a magnetic drive means disposed outside the casing and a magnetic attraction force adjustment means, wherein the impeller has a rotationally symmetric shape and is equipped with vanes having a pumping function on the side surface thereof and a magnetic means, such as permanent magnets on the bottom surface thereof, the magnetic drive means comprises a magnet assembly magnetically connected to the magnetic means and a rotation drive means for rotating the magnet assembly, the magnetic drive means rotates the impeller in cooperation with the magnetic means, and the magnetic attraction force adjustment means adjusts the magnetic attraction force generated between the magnetic means and the magnet assembly.

In addition, the blood pump of the present invention comprises an impeller, a casing having a suction inlet and a delivery outlet and rotatably encasing the impeller and a magnetic drive means disposed outside the casing, wherein the impeller has a rotationally symmetric shape and is equipped with vanes having a pumping function and a magnetic means, the magnetic drive means rotates the impeller in cooperation with the magnetic means., at least one of both ends of the rotation shaft of the impeller is supported by a pivot and a pivot bearing, and one of the pivot and the pivot bearing is made of ceramics and the other is made of synthetic resin.

The above-mentioned magnetic attraction adjustment means is a means for adjusting the gap between the magnetic means, such as permanent magnets, provided on the impeller and the magnetic drive means, such as permanent magnets rotated by a motor, disposed outside the casing opposite to the magnetic means, or a means for adjusting the exciting current of electromagnets when the magnetic drive means comprises electromagnets rotated by a motor. By adjusting the above-mentioned gap or exciting current, the magnetic attraction force generated between the magnetic means provided on the impeller and the magnetic drive means is adjusted. By this adjustment, the lifting force applied to the impeller, which varies depending on the pump operation conditions, such as rotation speed and flow rate, can be balanced properly with the magnetic attraction force which is also applied to the impeller. As a result, the rotation of the impeller can be maintained in an ideal weightless rotation condition., thereby causing less hemolysis during pump operation.

Furthermore, since the above-mentioned magnetic attraction force adjustment means performs axis alignment so that the rotation center axis of the magnetic means provided on the impeller is aligned with the center axis of the magnetic drive means, the adjustment means can be a means for moving the casing encasing the impeller in a horizontal plane, or a means for adjusting the inclination or verticality of the rotation center axis of the magnetic means. By the adjustment, the center axis of the magnetic means can be aligned with the center axis of the magnetic drive means, and the magnetic attraction force generated between the two means can be made uniform, thereby offering smooth and stable rotation of the impeller without causing vibration.

In the blood pump of the present invention wherein one of the pivot and the pivot bearing for supporting the rotation shaft of the impeller is made of ceramics and the other is made of synthetic resin, the amounts of wear of the pivot and the pivot bearing are significantly smaller than those of the conventional pivot and pivot bearing, thereby making stable pump operation possible for an extended period of time, and generating less hemolysis during operation.

DETAILED DESCRIPTION OF THE PREFERRED EMBODIMENTS

Figure 1:
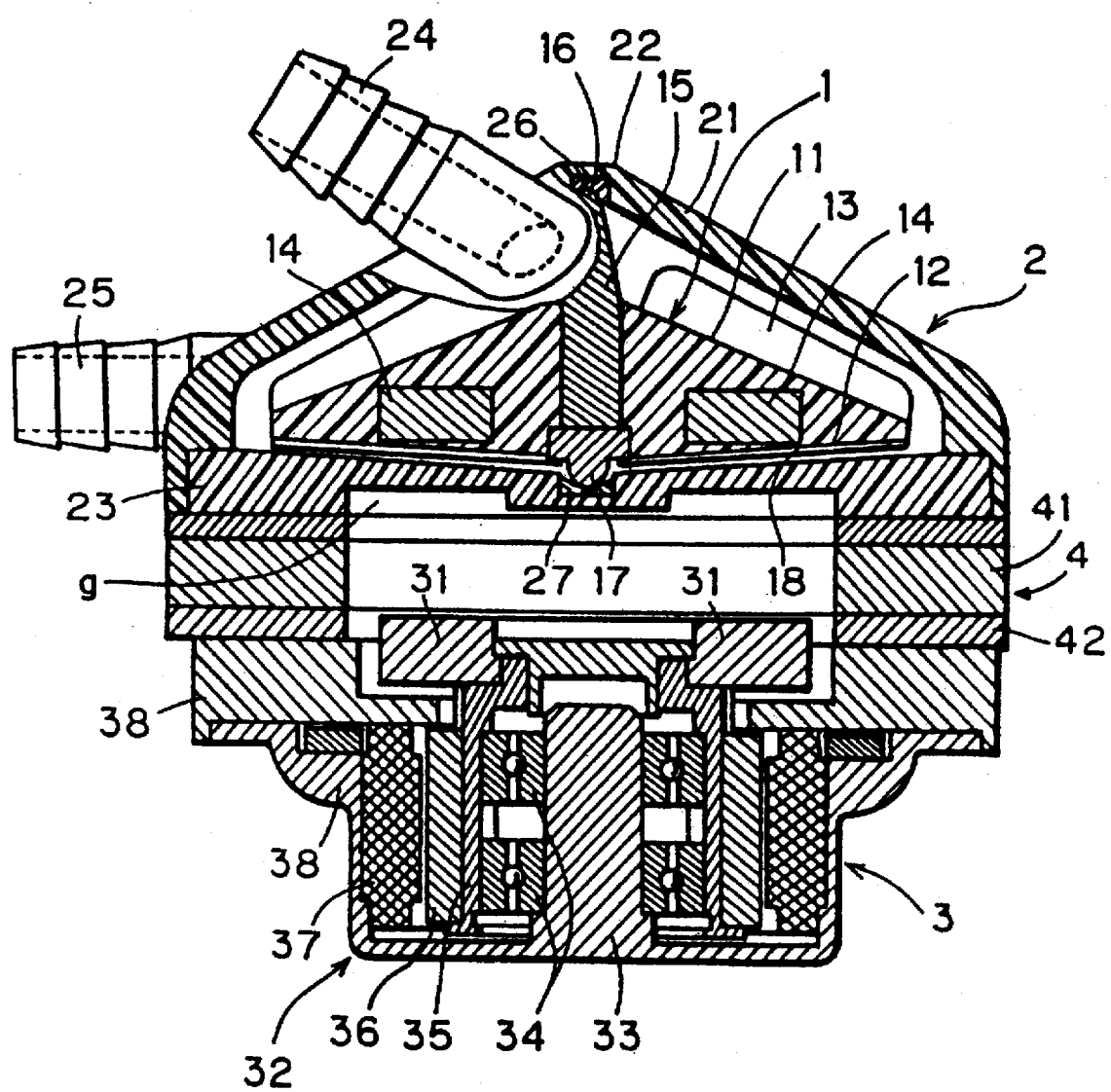
FIG. 1 is a vertical sectional view of a first embodiment of the blood pump of the present invention.
Figure 2:
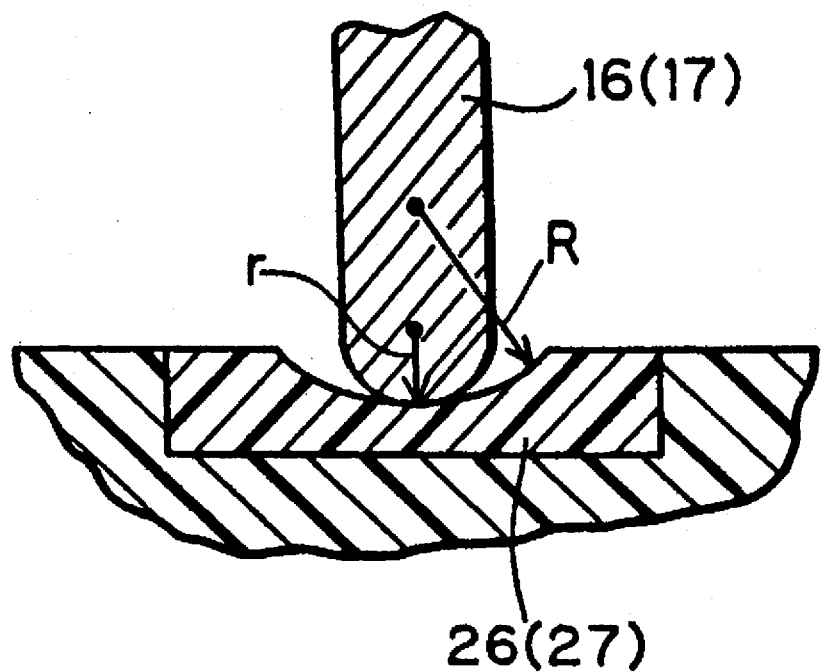
FIG. 2 is an enlarged sectional view illustrating a pivot and a pivot bearing.

FIG. 1 shows a first embodiment of the blood pump of the present invention. Numeral 1 represents an impeller rotatably encased in a casing 2. The impeller 1 has a nearly conical shape. The side surface 11 of the conical impeller 1 is provided with vanes 13. The vanes 13 have a pumping function of supplying blood sucked from a suction inlet 24 of the casing 2 to a delivery outlet 25 and delivering the blood from the delivery outlet 25 when the impeller 1 rotates. On the bottom surface side 12 of the impeller 1, a plurality of permanent magnets 14 constituting a magnetic means for rotating the impeller 1 are embedded symmetrically to the center axis of the rotation shaft 15 of the impeller 1. At the upper and lower ends of the rotation shaft 15 of the impeller 1, a pivot 16 and a pivot 17 are formed respectively. The pivot 16 is supported by a pivot bearing 26 embedded at the top of the conical section 21 of the casing 2. The pivot 17 at the lower end of the rotation shaft 15 is supported by a pivot bearing 27 embedded at the center of the bottom plate 23 of the casing 2. Either the pivot 16 or the pivot bearing 26 is made of ceramics, and the other is made of synthetic resin. Likewise, either the pivot 17 or the pivot bearing 27 is made of ceramics, and the other is made of synthetic resin. The curvature radii R of the bearing surfaces of the pivot bearings 26 and 27 are made larger than the curvature radii of the tips of the pivots 16 and 17 as shown in FIG. 2.

The suction inlet 24 is provided on the upper side (suction side) of the conical casing and extends in the direction nearly parallel to the inner surface of the conical section 21 of the casing 2 and the side surface 11 of the impeller 1 at a position eccentric from the top of the conical section. With this structure, the flow of blood sucked from the suction inlet 24 does not collide with the inner surface of the conical section 21 and the side surface 11 of the impeller 1, thereby preventing hemolysis. The delivery outlet 25 extends in the direction nearly parallel to the bottom side of the conical section 21 of the casing 2 (the delivery side of the casing). The casing 2 is sealed against liquid at the areas other than the delivery outlet. Numeral 18 represents auxiliary vanes provided on the bottom surface 12 of the impeller 1. The auxiliary vanes 18 are used to prevent blood from stagnating in the space between the bottom surface 12 of the impeller 1 and the bottom surface 23 of the casing 2. In the case of a type of blood pump placed outside the human body, the casing 2 should preferably be made of polycarbonate and the frame 38 of the magnetic drive means 3 should preferably be made of stainless steel. On the other hand, in the case of a type of blood pump embedded inside the human body, both the casing 2 and the frame 38 should preferably be made of a titanium alloy. The impeller 1 can be made of polyethylene, polypropylene, polymethyl acrylate or polycarbonate. As described later, either the pivot 16 or the pivot bearing 26 should preferably be made of ceramics and the other should preferably be made of synthetic resin. Likewise, either the pivot 17 or the pivot bearing 27 should preferably be made of ceramics and the other should preferably be made of synthetic resin.

Below the casing 2, a magnetic drive means 3 is provided. The magnetic drive means 3 is disposed opposite to the magnets 14 of the impeller 1. The magnetic drive means 3 comprises a magnet assembly 31 which rotates the impeller 1 in cooperation with the magnets 14 by magnetic connection with the magnets 14 and a rotation drive means 32 which coaxially rotates the magnet assembly 31 around the rotation center axis of the impeller 1. The magnet assembly 31 preferably comprises a plurality of permanent magnets, the number of which is identical to the number of magnets 14 constituting the magnetic means of the impeller 1 and which are disposed opposite to the magnets of the magnetic means with their polarities of the magnets thereof reversed from those of the magnets of the magnetic means so that the magnets of the magnet assembly 31 attract the magnets 14 of the magnetic means one another. Furthermore, the magnet assembly 31 is disposed symmetrically with respect to the center axis of the shaft 33 of the rotation drive means 32 and secured to the upper section of a rotor 35 supported by the shaft 33 via bearings 34, 34. The rotor 35 is such a rotor as that used for a DC brushless motor for example. Numeral 36 represents a rotor winding. The stator 37 of the motor is supported by a frame 38 and disposed close to the outer surface of the above-mentioned rotor. In this embodiment and all embodiments described below, a gap g is provided between the bottom plate 23 and the magnet assembly 31.

The blood pump of the present invention is provided with a magnetic attraction force adjustment means 4 between the casing 2 and the magnetic drive means 3 to adjust the magnetic connection, that is, magnetic attraction force generated between the magnets 14 of the magnetic means disposed on the impeller 1 and the magnet assembly 31. In the case of the blood pump shown in FIG. 1, the magnetic attraction force adjustment means 4 Comprises a supporting table 41 which is disposed below the casing 2 to support the casing 2 and a spacer 42 removably interposed between the Supporting table 41 and the frame 38 of the magnetic drive means 3 or between the supporting table 41 and the bottom surface of the casing 2 with the spacer 42 laminated on the supporting table 41. By inserting or removing a single or a plurality of spacers 42 having a proper thickness, the gap between the magnets 14 of the impeller 1 and the magnet assembly 31 of the magnetic drive means 3 disposed oppositely one another can be adjusted, and the magnetic connection, that is, magnetic attraction force generated between the magnets 14 and the magnets 31, can therefore be adjusted. By this adjustment, the lifting force applied to the impeller 1, which varies depending on the operation conditions of the blood pump can be properly balanced with the above-mentioned attraction force. As a result, the impeller can be rotated stably in the above-mentioned ideal conditions.

The casing 2, the magnetic drive means 3 and the magnetic attraction force adjustment means 4 are made contact with one another by the magnetic attraction force generated between the magnets 14 and the magnet assembly 31. However, a connection means (not shown) can be provided externally when necessary. When the casing 2, the magnetic drive means 3 and the magnetic connection adjustment means 4 are removably connected just as in the case of this embodiment, the casing 2 and the impeller 1 in the casing 2 can be made disposable, and the magnetic drive means 3 and the magnetic connection adjustment means 4 can be used repeatedly.

Figure 3:
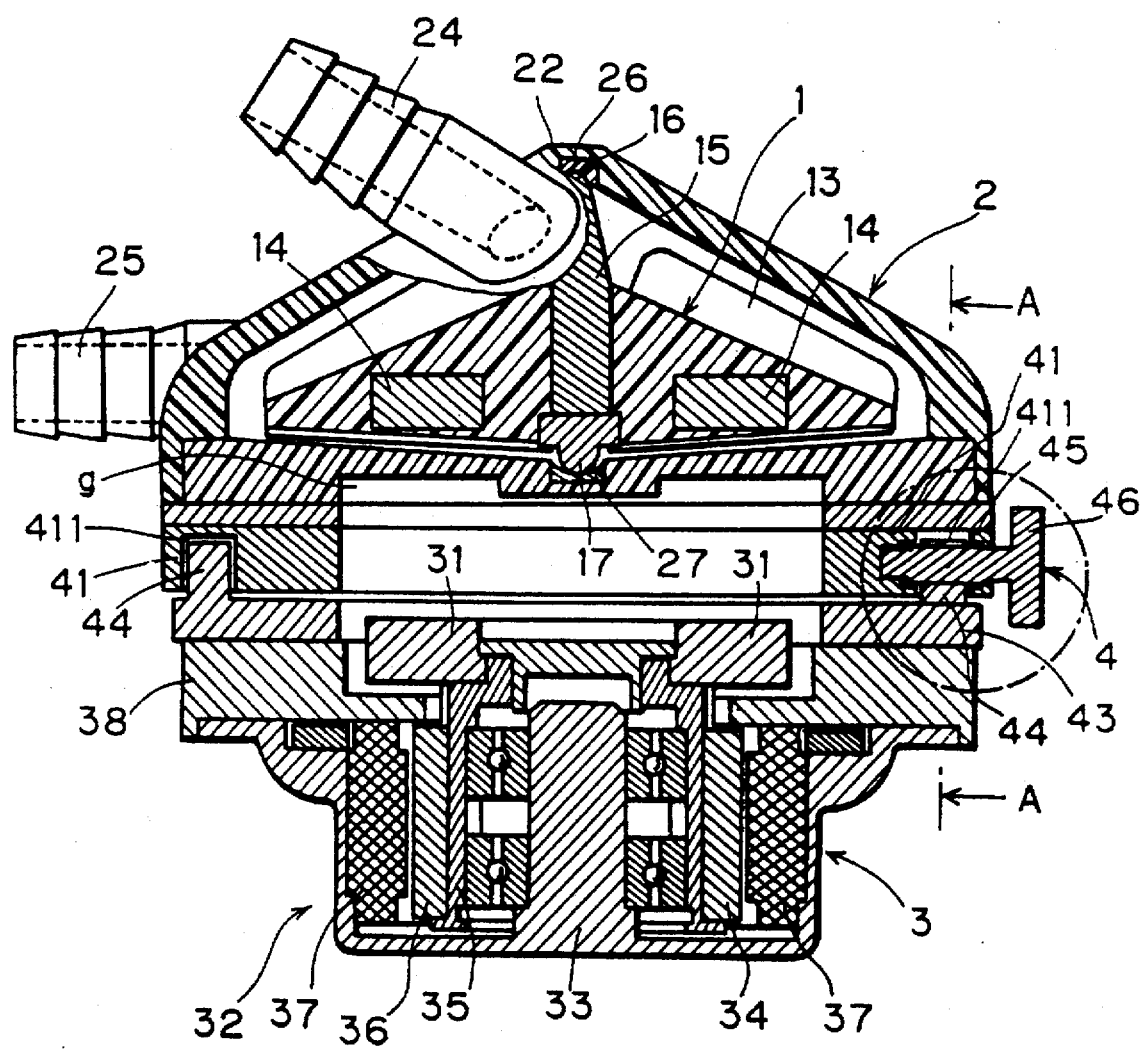
FIG. 3 is a vertical sectional view of a second embodiment of the blood pump of the present invention.
Figure 4:
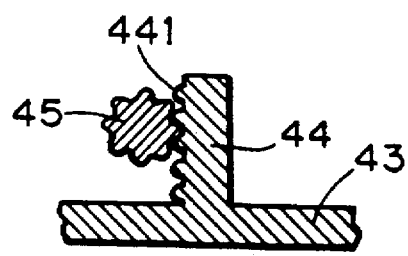
FIG. 4 is an enlarged sectional view illustrating a guide rod and a gear, taken on line A—A of FIG. 3.

In a second embodiment of the present invention shown in FIGS. 3 and 4, the impeller 1, casing 2 and magnetic drive means 3 are the same as those described above in the first embodiment. Only the structure of the magnetic attraction force adjustment means 4 differs from that of the adjustment means of the above mentioned first embodiment. In the second embodiment, the supporting table 41 for supporting the casing 2 has a plurality of guide holes 411 vertically extending from the bottom surface thereof. A plurality of guide rods 44 projecting from the base 43 mounted on the magnetic drive means 3 are inserted into the above-mentioned guide holes 411. At least one of the guide rods 44 is provided with a screw thread 441 provided on the side surface thereof and extending horizontally to almost the entire length of the rod. A gear 45 engaging the screw thread 441 is disposed on the supporting table 41. By rotating a knob 46 connected to the gear 45, the gear 45 is moved vertically in the rack-pinion method. The supporting table 41 connected to the gear 45 is thus moved vertically with respect to the base 43. By this movement, the gap between the magnets 14 of the impeller 1 and the magnet assembly 31 of the magnetic drive means 3 can be adjusted, and the magnetic attraction force generated between the magnets 14 and the magnets 31 can be adjusted. The adjustment of the magnetic attraction force in the second embodiment is advantageous, since the adjustment can be done during operation of the blood pump.

Figure 5:
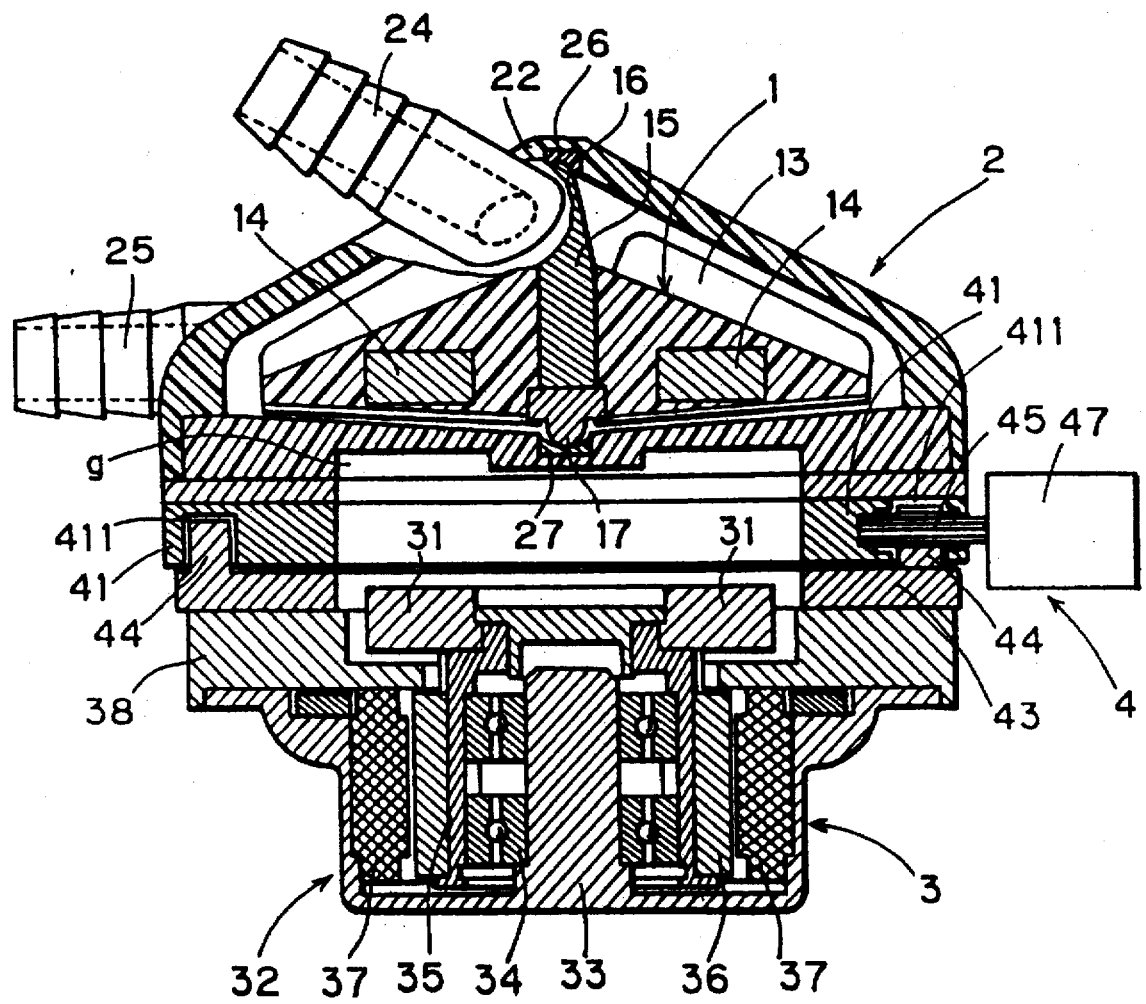
FIG. 5 is a vertical sectional view of a third embodiment of the blood pump of the present invention.
Figure 6:
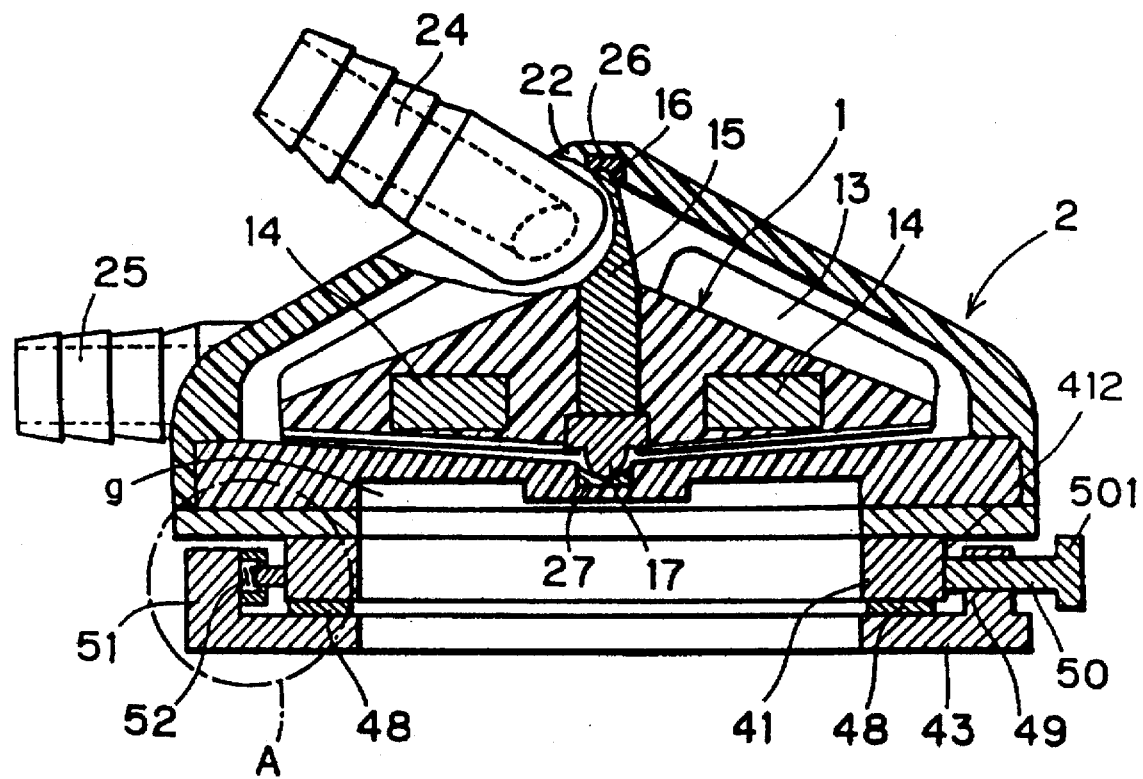
FIG. 6 is a partly-omitted vertical sectional view of a fourth embodiment of the blood pump of the present invention.
Figure 7:
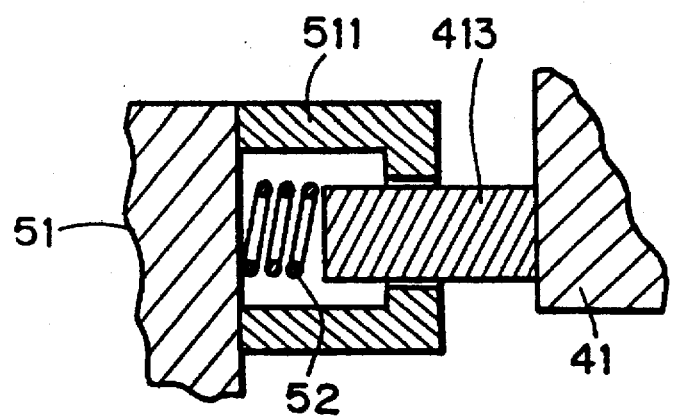
FIG. 7 is an enlarged view of portion A of FIG. 6.

Instead of turning the knob 46 in the case of the second embodiment, a stepping motor 47 is used to rotate the gear 45 in the case of a third embodiment shown in FIG. 5. The gap between the magnets 14 and the magnets 31 can be controlled optimally by feeding back information such as rotation speed, torque, flow rate, vibration of the blood pump to the control section (not shown) of the stepping motor 47. In FIGS. 6 and 7 illustrating a fourth embodiment, the magnetic drive means 3 is not shown to make the drawings simple. The impeller 1 and the casing 2 are the same as those of the above-mentioned embodiments. In the fourth embodiment, the supporting table 41 for supporting the casing 2 is mounted on a flat-plate-shaped guide rail 48 on the base 43. The tip of a traverse screw 50 engaging a thread hole (not shown) in a stand 49 vertically projecting from the base 43 is in contact with the side surface 412 of the supporting table 41. On the side surface opposite to the above-mentioned contact section in the extension direction of the above-mentioned traverse screw 50, a rod 413 extending in the extension direction of the traverse screw 50 is projecting. The tip of the rod 413 presses a spring 52 inserted into the spring accommodation section 511 provided on the side surface of the stand 51 projecting vertically from the base 43. With this structure, by turning the knob 501 of the traverse screw 50 and by moving the screw 50 forward or backward toward the supporting table 41, the supporting table 41 can be moved horizontally in the X direction. A horizontal movement means similar to the above-mentioned movement means is also provided in the Y direction. By horizontally moving the supporting table 41 in the X and Y directions, the rotation center axis of the magnets 14 of the impeller 1 in the casing 2 supported on the supporting table 41 can be aligned with the rotation center axis of the magnet assembly 31 of the magnetic drive means 3.

Figure 8:
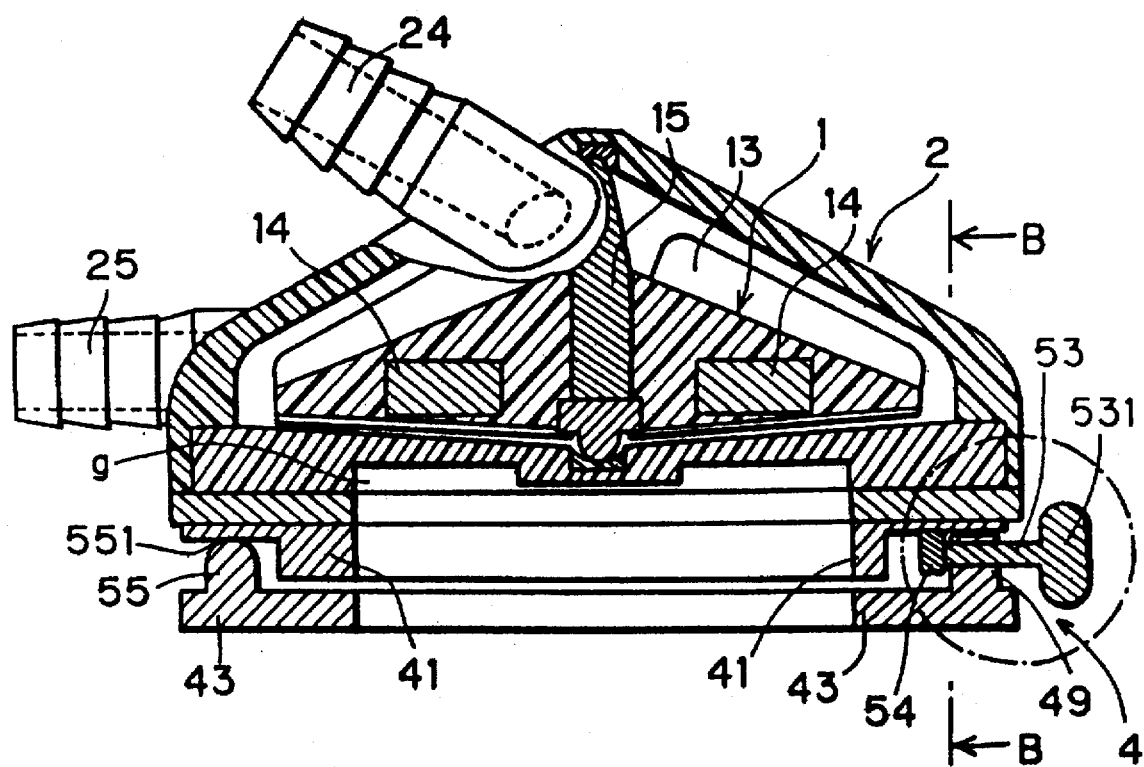
FIG. 8 is a partly-omitted vertical sectional view of a fifth embodiment of the blood pump of the present invention.
Figure 9:
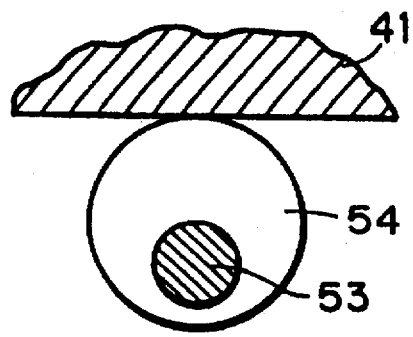
FIG. 9 is an enlarged sectional view illustrating an eccentric cam, taken on line B—B of FIG. 8.

In FIGS. 8 and 9 illustrating a fifth embodiment, the magnetic drive means 3 is not shown either. In the blood pump shown in FIG. 8, an eccentric cam 54 is mounted at the tip of a shaft 53 engaging a thread hole (not shown) in a stand vertically projecting from the base 43. By rotating the eccentric cam 54, the supporting table 41 for supporting the casing 2 is partially moved vertically, and the inclination of the table 41 to the horizontal plane is adjusted. By this adjustment, the inclination of the rotation shaft 15 of the impeller 1 can be adjusted. The top 551 of a stand 55 used as a fulcrum for adjusting the inclination of the supporting table 41 has a hemispheric shape. Numeral 531 represents a knob used to rotate the eccentric cam 54.

By using the adjustment means shown in FIGS. 6 and 7, and the adjustment means shown in FIGS. 8 and 9, the rotation center axis of the impeller 1 can be aligned with the center axis of the magnetic drive means 3, and the magnetic attraction force generated between the magnets 14 of the impeller 1 and the magnet assembly 31 of the magnetic drive means 3 can be adjusted to a uniform value. As a result, the impeller 1 can be rotated stably for an extended period of time without generating vibration.

In the blood pump of the present invention, the above-mentioned means for adjusting the position and inclination of the rotation center axis can be used with one of the above-mentioned adjustment means shown in FIGS. 1 to 5, which are used to adjust the gap (magnet gap) between the magnets 14 and the magnets 31.

Figure 10:
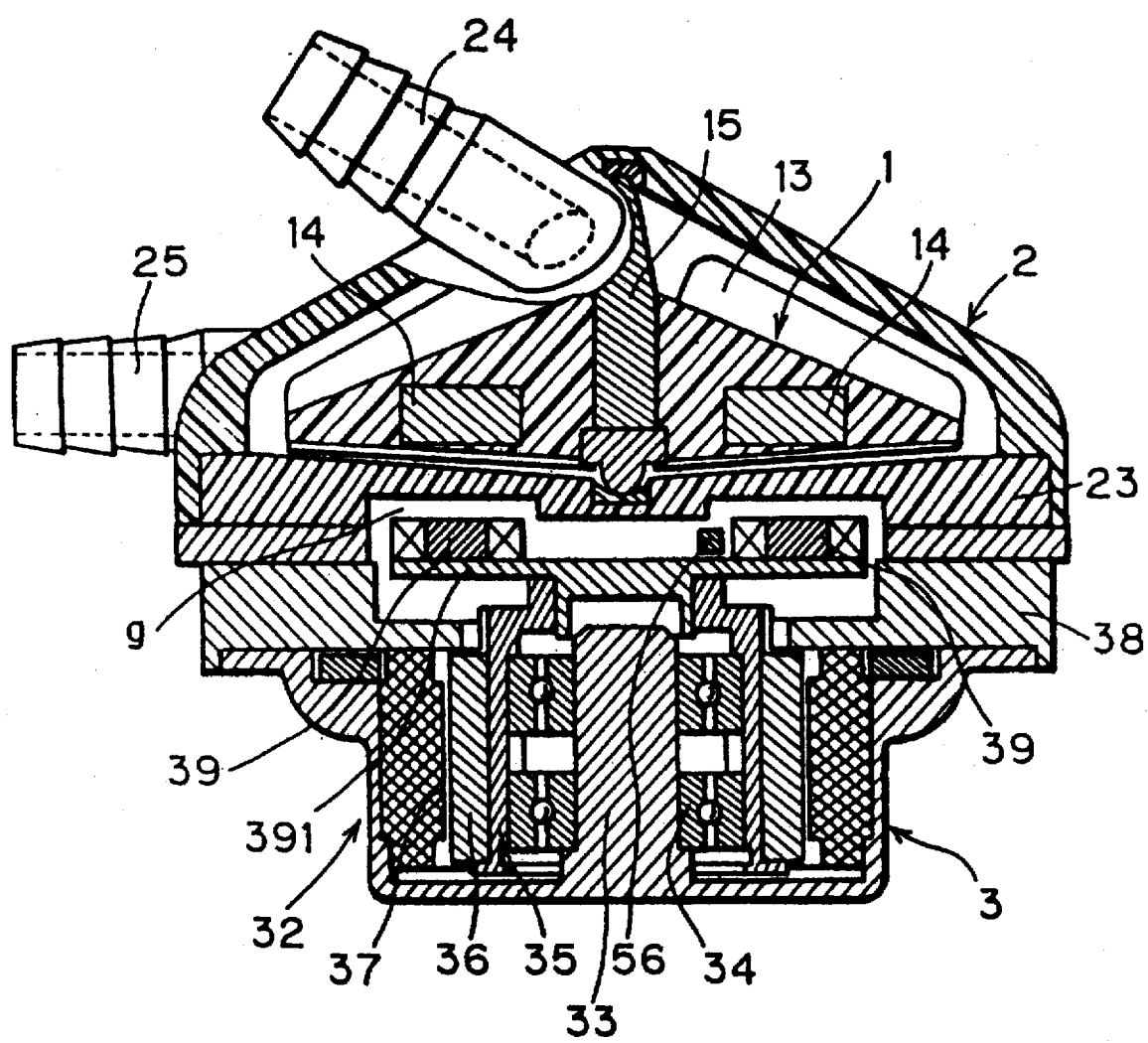
FIG. 10 is a vertical sectional view of a sixth embodiment of the blood pump of the present invention.

In a sixth embodiment shown in FIG. 10, electromagnets 39 secured onto a disc 391 which is made unrotatable with respect to the casing 2 by a rotation prevention means (not shown), such as a screw or a locking member, are provided instead of the permanent magnets 31 of the magnetic drive means 3, which are used in the first to fifth embodiments. The magnetic attraction force generated between the magnets 14 of the impeller 1 and the electromagnets 39 is adjusted by changing the exciting current of the electromagnets 39. In this case, one of the magnet gap adjustment means shown in FIGS. 1 to 5 can be used together. Numeral 56 in FIG. 10 represents a hole sensor used to detect rotation speed or the like and secured onto the disc 391 as well as electromagnets 39. Although not shown as a developed embodiment of the present invention, electromagnets can be provided on the upper section of the casing 2 so that the electromagnets can generate a magnetic field to repulse the magnetic force of the magnets disposed in the impeller 1 when the rotation speed of the impeller 1 increases and the impeller 1 begins to be lifted, thereby assisting in setting the impeller 1 to a weightless condition.

Test Results

Figure 11:
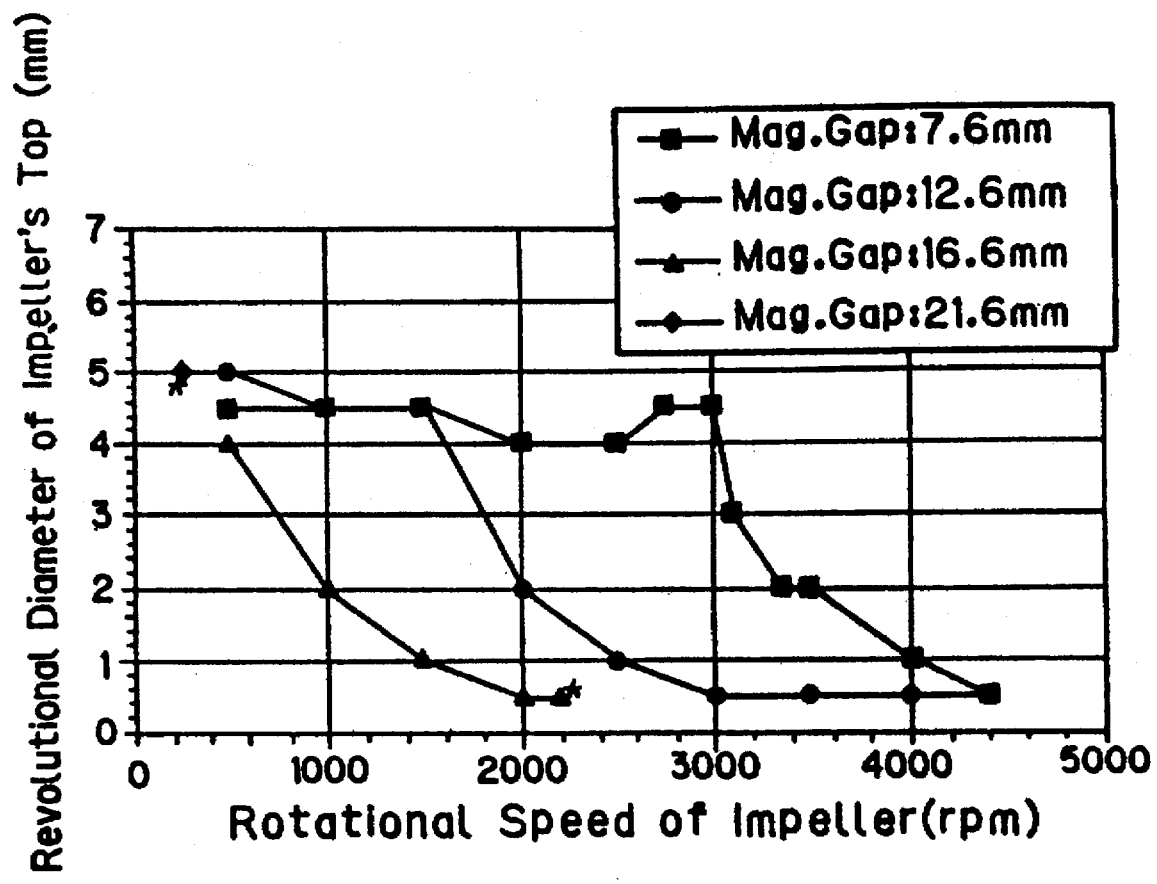
FIGS. 11, 12 and 13 are graphs illustrating the relationships between the magnet gap and the revolution diameter at the top of the impeller, between the magnet gap and casing vibration, and between the magnet gap and the amount of hemolysis.

Blood pumps having different magnet gaps between the magnets 14 of the impeller 1 and the magnets 31 of the magnetic drive means 3 were prepared by using the above-mentioned means, and the relationship between the rotation speed of the impeller and the revolution diameter at the top of the rotation shaft of the impeller, that is, at the top of the upper pivot was measured. The results of the measurement are shown in FIG. 11. The revolution diameter indicates vibratory rotation of the top of the upper pivot and should preferably be smaller. FIG. 11 shows that the magnet gap for minimizing the revolution diameter differs depending on the rotation speed of the impeller. As the rotation speed increases, it is indicated that the magnet gap should be decreased. In FIG. 11, the star mark indicates a condition wherein the rotation torque of the magnets of the magnetic drive means cannot be transmitted to the magnets of the impeller, and this condition is referred to as "decoupling." Decoupling is apt to occur when the magnet gap is larger.

Figure 12:
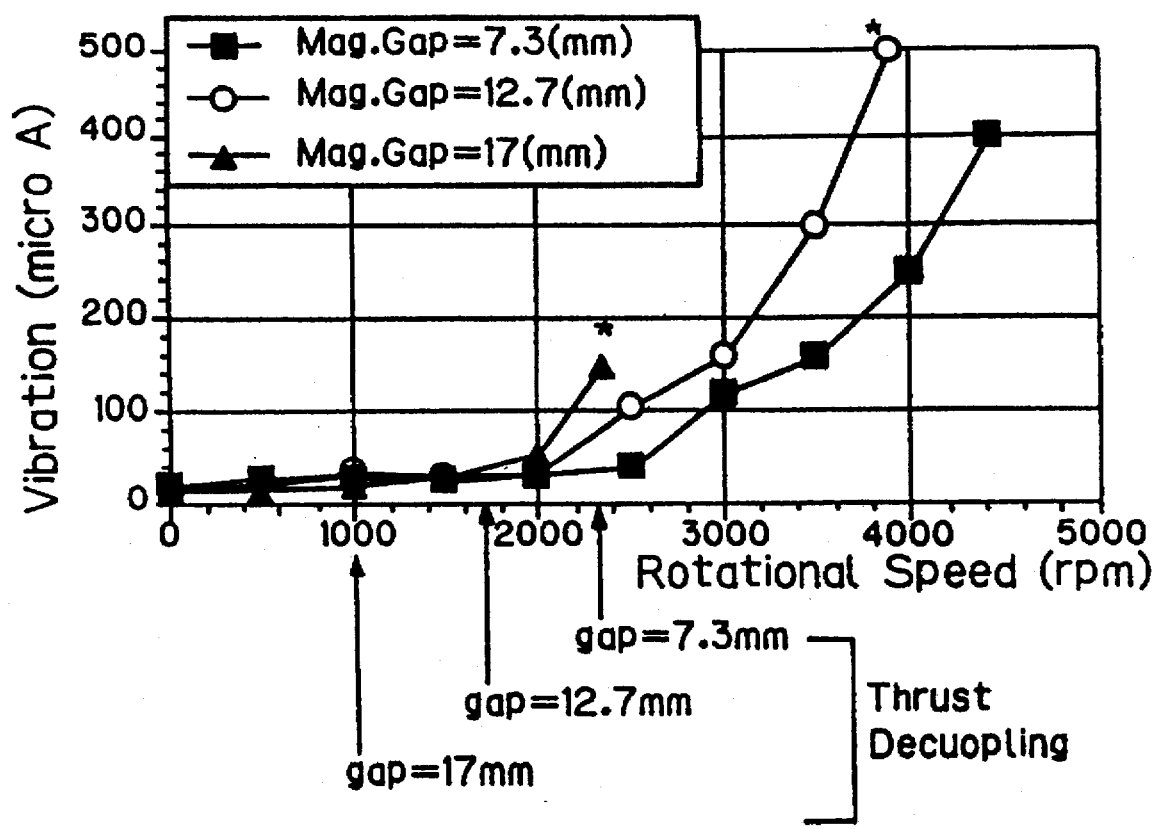

Next, the relationship between the rotation speed of the impeller and the magnitude of vibration generated on the casing was examined by using blood pumps having different magnet gaps. The magnitude of vibration at the axis of ordinate in FIG. 12 is indicated by the reading of current values measured by a vibration meter. Vibration increases as the current value becomes larger. FIG. 12 shows that as the gap is smaller, the magnitude of vibration is less even at higher rotation speed. In any values of magnet gaps, the impeller is supported by the pivot bearing disposed at the bottom when rotation speed is low. When rotation speed becomes higher, lifting force is applied to the impeller, and the impeller becomes to be supported by the pivot bearing located at the top of the impeller. This transfer of bearings used for supporting the impeller is referred to as "thrust decoupling." When the rotation speed increases further, the magnitude of vibration increases abruptly. The rotation speed obtained just before or after thrust decoupling occurs is close to a speed corresponding to a weightless condition and offers an optimal rotation condition with low vibration. However, as the magnet gap is larger, the rotation speed offering the optimal rotation condition is lower, and as the magnet gap is smaller, the rotation speed offering the optimal rotation condition is higher.

Figure 13:
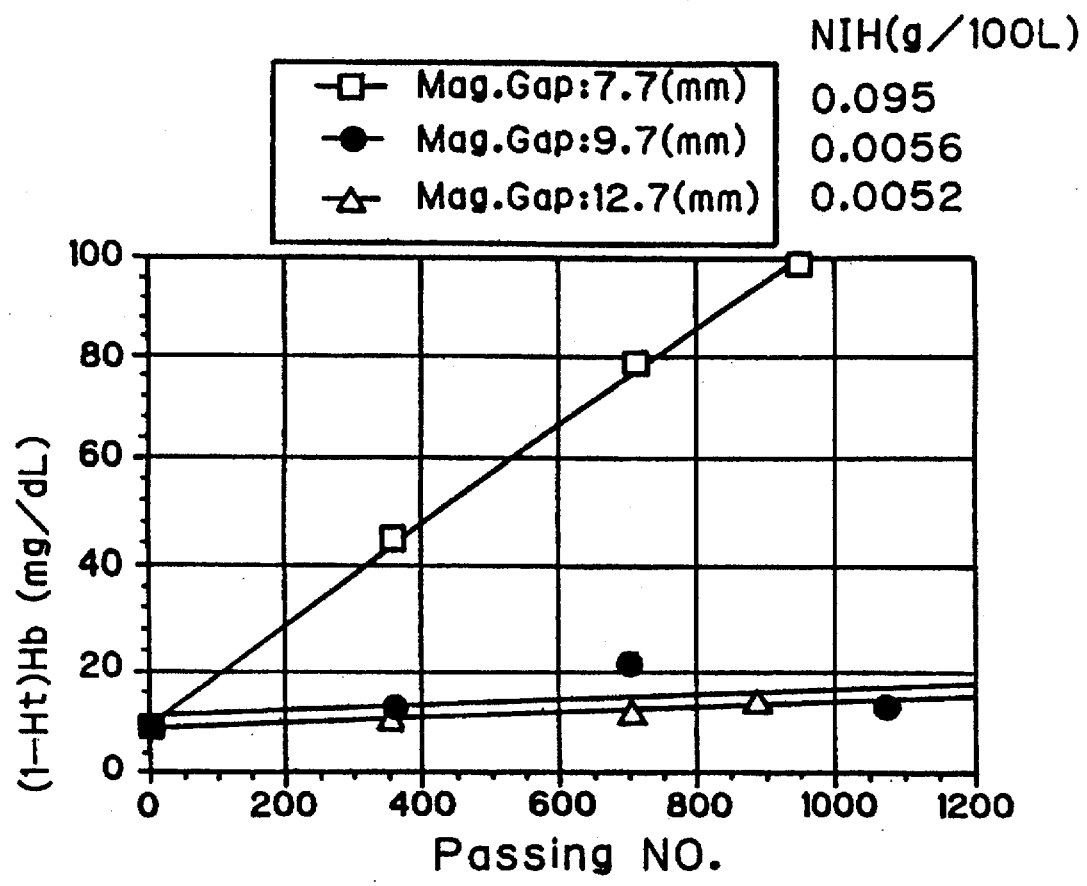

Furthermore, the relationship between the number of repetitive passings of bovine blood to blood pumps rotating at 1911 rpm and the amount of hemolysis, that is, the amount of hemoglobin discharged from destroyed red blood cells was measured by using blood pumps with different magnet gaps, and the results shown in FIG. 13 were obtained. On the basis of this graph, the hemolysis index NIH value corresponding to the inclination of each characteristic straight line was obtained by calculation and the values indicated in FIG. 13 were obtained. Since the hemolysis index differs depending on the magnet gap, it is necessary to select a magnet gap which brings about a low hemolysis index value.

As described above, in the blood pump of the present invention, it is preferable that one of the pivot and pivot bearing for supporting the upper end and/or lower end of the rotation shaft of the impeller is made of ceramics, and that the other is made of synthetic resin. In this case, alumina, zirconia, silicon carbide, silicon nitride, etc. can preferably be used as ceramics. Ceramics having a bending strength of 400 MPa or more, a Vickers hardness of 1000 kg/mm$^2$ or more, a Young's modulus of 200 GPa or more and a thermal expansion coefficient of $15 \times 10^{-6}$° C. or less at temperatures of 40° to 400° C. are used preferably. As synthetic resin, high-density polyethylene, polycarbonate, polytetrafluoroethylene, etc. can be used preferably. Synthetic resin having a tensile strength of 2 to 7 kg/mm$^2$, an elongation of 15 to 500% and a tensile elastic modulus of 40 to 250 kg/mm$^2$ are used preferably. The surface roughness of the pivot should preferably be 0.2 to 1.5μm and the curvature radius of the tip of the pivot should preferably be 0.5 to 10 mm.

When the upper and lower sections of the rotation shaft of the impeller of the blood pump of the present invention were supported by the pivots and pivot bearings made of the materials shown in Table 1, an experiment was conducted to examine the wear of the pivot and pivot bearing.

TABLE 1

| Attribute | Item | |
|---|---|---|
| | Pivot | Pivot bearing |
| Example of present invention | Silicon carbide | High-density polyethylene |
| Example for comparison | Silicon carbide | Silicon carbide |

Bovine blood was used for the experiment. After the two types of pumps were operated continuously for 18 hours at a pump rotation speed of 2,500 rpm, a flow rate of 5 litters/minute and a total head of 350 mmHg, the total amount of wear of the upper and lower pivots and pivot bearings was measured. In the case of the example for comparison, the total amount of wear reached 180 μm and looseness was detected between the impeller and the casing, and the impeller rattled. In the case of the example of the present invention, however, the total amount of wear was nearly zero, no looseness or rattling was detected, and no noise was generated by impeller rotation.

Next, the combinations of the materials for the Upper and lower pivots and pivot bearings for supporting the rotation shaft of the impeller were selected as shown in Table 2.

TABLE 2

| Attribute | Item | |
|---|---|---|
| | Pivot | Pivot bearing |
| Example of present invention | Alumina | High-density polyethylene |
| Example for comparison | Silicon carbide | Silicon carbide |

Figure 14:
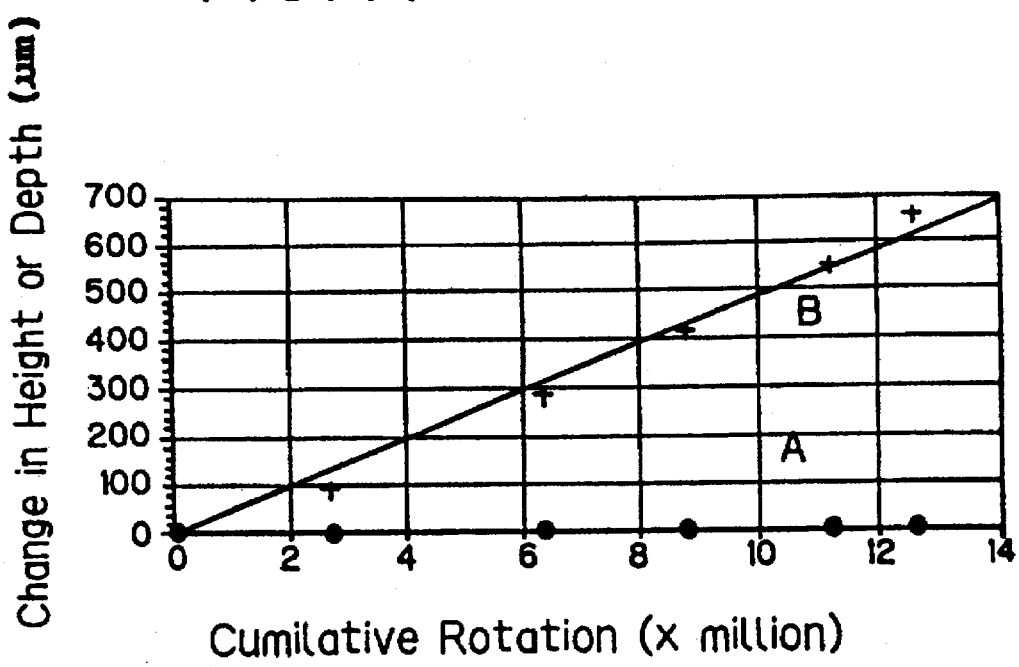
FIGS. 14 and 15 are graphs illustrating the comparison of the blood pump of the present invention and a conventional blood pump in terms of performance.

By also using bovine blood and by operating the two types of pumps at a pump rotation speed of 1550 rpm, a flow rate of 5 litters/minute and a total head of 90 mmHg, the relationship between the cumulative rotation and the total amount of wear was measured. The results were shown in FIG. 14. Straight line A indicates the total amount of wear in the example of the present invention and straight line B indicates the total amount of wear in the example for comparison. As is evident from FIG. 14, the amount of wear is extremely small in the example of the present invention. Although the wear rate ($10^{-6}$ μm/rotation) of the example for comparison is 51.1, the wear rate of the example of the present invention is 0.71.

Figure 15:
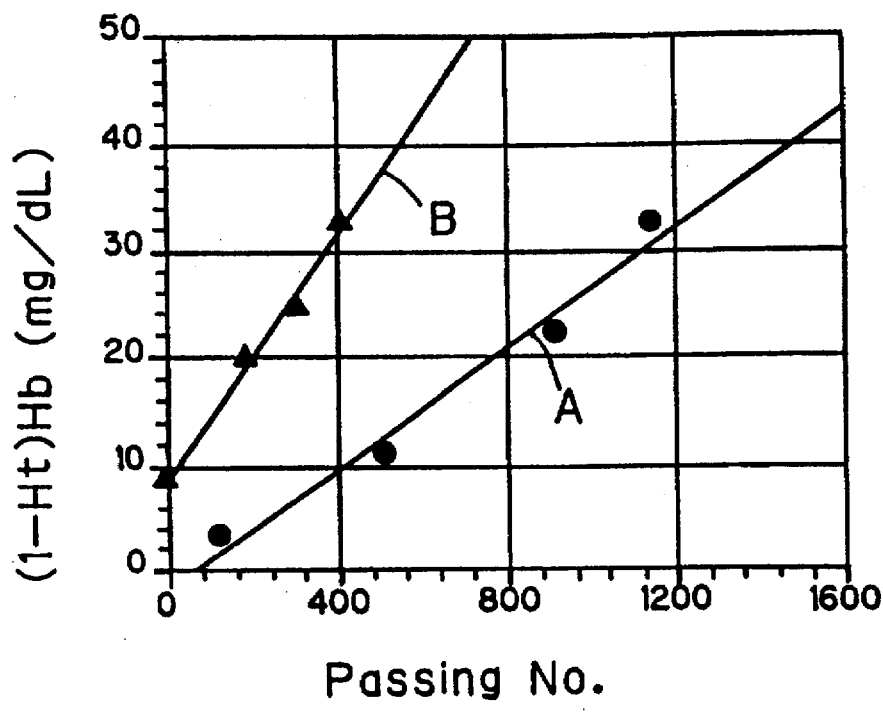

Furthermore, blood was passed repeatedly through the two types of blood pumps in the same conditions as those used for the experiment corresponding to Table 1, and the relationship between the number of passings and the amount of hemoglobin in blood was measured. The results of the measurement were shown in FIG. 15. Straight line A indicates the results of the example of the present invention and straight line B indicates the results of the example for comparison. From this graph, hemolysis index NIH values were obtained by calculation. The index value for the example for comparison was 0.057 (g/100 litters) and the index value for the example of the present invention was 0.028 (g/100 litters). It is assumed that the amount of hemolysis is reduced in the example of the present invention since impeller vibration is little.

The above-mentioned blood pump of the present invention can be changed or modified as described below. Instead of supporting the upper or lower end of the impeller, or both ends thereof, the impeller may be rotatably supported by at least three rotation balls on the bottom plate of the casing, or the side surface of the upper side of the impeller may be supported by at least three rotation balls, Furthermore, the suction inlet of the casing may be extended in parallel with the rotation center axis of the impeller at a position eccentric from the top of the conical casing. Moreover, the blood pump of the present invention can be changed or modified variously within the spirit and scope of the present invention.

We claim:

1. A blood pump comprising:

a rotationally symmetric impeller comprising a plurality of vanes, magnetic means for rotating the impeller, and a rotational shaft having at least one end supported by a pivot and a pivot bearing, the pivot and the pivot bearing being mutually slidable, one of the pivot and the pivot bearing comprising a ceramic and the other one of the pivot and the pivot bearing comprising a synthetic resin, a casing in which the impeller is rotatably encasable, the casing having an inlet and an outlet, and magnetic drive means disposed outside the casing for rotating the impeller in cooperation with the magnetic means.

* * * * *

UNITED STATES PATENT AND TRADEMARK OFFICE
CERTIFICATE OF CORRECTION

PATENT NO. : 5,683,231
DATED : November 4, 1997
INVENTOR(S) : TADASHI NAKAZAWA ET AL.

It is certified that error appears in the above-indentified patent and that said Letters Patent is hereby corrected as shown below:

On the title page: Item [73]            insert --BAYLOR COLLEGE OF MEDICINE, Houston, Texas-- as the second Assignee.

Signed and Sealed this

Twenty-sixth Day of May, 1998

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,683,231
DATED : November 4, 1997
INVENTOR(S) : TADASHI NAKAZAWA et al.

It is certified that error appears in the above-identified patent and that said Letters Patent is hereby corrected as shown below:

Title page, item [73] Assignee: add --BAYLOR COLLEGE OF MEDICINE, Houston, Texas--.

Signed and Sealed this

Ninth Day of June, 1998

Attest:

BRUCE LEHMAN

Attesting Officer

Commissioner of Patents and Trademarks